United States Patent [19]

Ogawa et al.

[11] Patent Number: 4,537,999
[45] Date of Patent: Aug. 27, 1985

[54] PROCESS FOR A PRODUCTION OF DINITROPHENYL ETHERS

[75] Inventors: Tetsuya Ogawa; Shinichi Saitoh, both of Chibaken; Takeshi Inoi, Kanagawaken; Masaji Kato, Shizuokaken; Heitaro Obara, Miyagiken, all of Japan

[73] Assignees: Chisso Corporation, Osaka; Kaken Pharmaceutical Co., Ltd., Tokyo, both of Japan

[21] Appl. No.: 534,145

[22] Filed: Sep. 21, 1983

[30] Foreign Application Priority Data

Sep. 30, 1982 [JP] Japan ................... 57-172265

[51] Int. Cl.³ ............... C07C 41/14; C07C 79/35
[52] U.S. Cl. .................. 568/584; 568/585; 568/586
[58] Field of Search ............... 568/584, 585, 586

[56] References Cited

PUBLICATIONS

Gitis et al., Chem. Abs., vol. 52, (1956), 20009(a).

Primary Examiner—Bernard Helfin
Attorney, Agent, or Firm—Wenderoth, Lind & Ponack

[57] ABSTRACT

A process for the production of dinitrophenyl ethers having the general formula [III]:

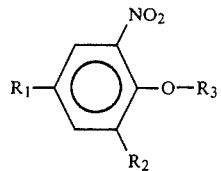

wherein, one of $R_1$ and $R_2$ is a nitro radical, and the other is a hydrogen atom or a straight-chain, branched-chain or cyclic, saturated or unsaturated hydrocarbon radical containing from 1 to 10 carbon atoms, and $R_3$ is a radical selected from the group consisting of (i) a straight-chain, branched-chain or cyclic, saturated or unsaturated hydrocarbon radical containing from 2 to 10 carbon atoms, (ii) a straight-chain hydrocarbon radical having one phenyl group as a substituent and containing from 1 to 5 carbon atoms, (iii) a phenyl radical, and (iv) a phenyl radical with one or more than one substituents selected from the group consisting of a nitro group, a halogen group, a saturated or unsaturated hydrocarbon group containing from 1 to 5 carbon atoms and an alkoxy group containing from 1 to 4 carbon atoms, by reacting a compound represented by the formula [I]:

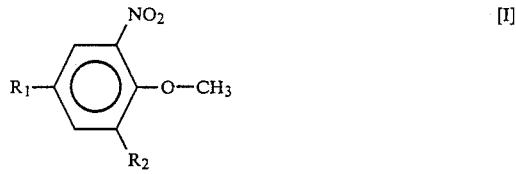

wherein, $R_1$ and $R_2$ have the above-mentioned meanings, and a compound represented by the general formula [II]:

$R_3OH$  [II]

wherein, $R_3$ has the above-mentioned meaning, in the presence of an alkaline compound. This process has greater ease compared with the classical synthetic processes using a halogen compound intermediate.

3 Claims, No Drawings

PROCESS FOR A PRODUCTION OF DINITROPHENYL ETHERS

BACKGROUND OF THE INVENTION

This invention relates to a process for the production of dinitrophenyl ethers, and more particularly to the process for the production of dinitrophenyl ethers represented by the following general formula [III]:

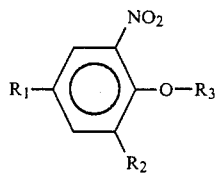

wherein, one of $R_1$ and $R_2$ is a nitro radical, and the other is a hydrogen atom or a straight-chain, branched-chain or cyclic saturated or unsaturated hydrocarbon radical containing from 1 to 10 carbon atoms, and $R_3$ is a radical selected from the group consisting of (i) a straight-chain, branched-chain or cyclic, saturated or unsaturated hydrocarbon radical containing from 2 to 10 carbon atoms, (ii) a straight-chain hydrocarbon radical having one phenyl group as a substituent and containing from 1 to 5 carbon atoms, (iii) a phenyl radical, and (iv) a phenyl radical with one or more than one substituents selected from the group consisting of a nitro group, a halogen group, a saturated or unsaturated hydrocarbon group containing from 1 to 5 carbon atoms and an alkoxy group containing from 1 to 4 carbon atoms.

Dinitrophenyl ethers obtained by the process according to the invention include known compounds and novel compounds. As such dinitrophenyl ethers, for example, 2,4-dinitrophenyl ether is described in British Patent Specification No. 1279874 (1969), and 2,6-dinitrophenyl ether is described in Japanese Open-laid Patent Specification No. SHO 56-2901 (1981). These prior literature references are, however, related to the activities of the corresponding dinitrophenyl ether compounds as agricultural chemicals, and the synthetic processes for preparation of these compounds are not studied. The synthetic process described in the said British Patent is, therefore, only to carry out the general classic known processes (described later). The said general known processes are the following two:

(1) a process for reacting dinitrophenols and a halogenated hydrocarbon in the presence of an equal molar or more than equal molar alkali, and (2) a process for reacting dinitrohalobenzene and an alcohol in the presence of strong alkaline liquid. In both processes, therefore, it is necessary to prepare the halogenated compounds beforehand and to use a large quantity of the alkaline substances. Furthermore, the above-mentioned two processes have a disadvantage such that the synthesis of the compounds having as $R_3$ a phenyl radical with a substituent as in the above-mentioned formula [III] is not possible.

Because of the above-mentioned conditions, if any compound having a high activity as agricultural chemicals is found among dinitrophenyl ethers in the future, it is difficult to produce that compound advantageously from the viewpoint of economics. The inventors have studied to solve the above-mentioned technical problems concerning the process for production of dinitrophenyl ethers. Consequently, they have found that the objective compounds can be obtained more easily as to their procedures and also in better yield than the classic processes, by using dinitrophenyl methyl ether and the specified alcohol as raw materials as well as a catalytic amount of an alkaline compound.

As seen clearly from the aforesaid description, the invention provides novel synthetic process of preparing dinitrophenyl ethers without using any halogen compound as an intermediate. Another object is to provide the said synthetic process by which the objective compounds can be obtained in higher yield than the conventional processes which use a halogen compound as an intermediate. The other objects will become clear from the following description.

SUMMARY OF THE INVENTION

This invention has the following main constitution (1) and (2).

(1) A process for production of dinitrophenyl ethers represented by the general formula [III]:

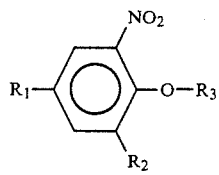

wherein, one of $R_1$ and $R_2$ is a nitro radical, and the other is a hydrogen atom or a straight-chain, branched-chain or cyclic, saturated or unsaturated hydrocarbon radical containing from 1 to 10 carbon atoms, and $R_3$ is a radical selected from the group consisting of (i) a straight-chain, branched-chain or cyclic, saturated or unsaturated hydrocarbon radical containing from 2 to 10 carbon atoms, (ii) a straight-chain hydrocarbon radical having one phenyl group as a substituent and containing from 1 to 5 carbon atoms, (iii) a phenyl radical, and (iv) a phenyl radical with one or more than one substituents selected from the group consisting of a nitro group, a halogen group, a saturated or unsaturated hydrocarbon group containing from 1 to 5 carbon atoms and an alkoxy group containing from 1 to 4 carbon atoms, characterized by reacting a compound represented by the general formula [I]:

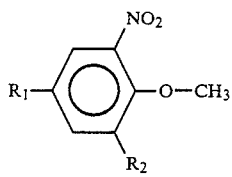

wherein, $R_1$ and $R_2$ have the above-mentioned meanings, and a compound represented by the general formula [II]:

$R_3OH$         [II]

wherein, $R_3$ has the above-mentioned meaning, in the presence of an alkaline compound.

(2) A process as described in (1), characterized by conducting the reaction in the presence or absence of an inert solvent.

Compounds represented by the general formulae [I] and [II] used in the invention can be prepared from known starting compounds by known methods. Examples of the alkaline compounds to be used as the catalyst are inorganic compounds such as NaOH, KOH, Na$_2$CO$_3$ and K$_2$CO$_3$, as well as organic amines such as monoethylamine, diethylamine and pyridine. These alkaline compounds are used in a quantity of $\frac{1}{2} \sim 1/10$ moles per mole of the compound represented by general formula [I]. The quantitative ratio of compounds represented by general formulae [I] and [II] used may be the theoretical one, i.e. the equal molar ratio, and it may be also possible to use either excess to the other by $0.1 \sim 0.5$ moles. In that case, the more easily recoverable compound is used in excess.

In carrying out the process, any solvent which is inert to the reactants and the product, such as benzene, hexane, toluene or xylene, etc., may be used in a quantity of $0.1 \sim 10$ moles, preferably $0.5 \sim 5$ moles, per mole of reactants (i.e. total quantity of compounds represented by general formulae [I] and [II]). However, in the case that the compound represented by general formula [II] is liquid at from room temperature to the reaction temperature, the reaction of the invention may be carried out without using any solvent. In the case of the process being carried out under a normal pressure, the reaction temperature may be limited to the boiling temperature of the used solvent or the compound represented by general formula [II], but in the case where the aforesaid limitation is not present, it is possible to select the preferred temperature within the range between 60° and 180° C. Further, it is allowed to carry out the process under an excess pressure, such as one within the range between 0 and 5 Kg/cm$^2$G. Although the reaction period is not limited, in most cases to complete the process it takes from 1 to 4 hours after the reaction temperature is attained. To separate the objective compound (i.e. dinitrophenyl ethers represented by general formula [III]) from the reaction mixture after the end of the reaction, filtration, washing, and recrystallization, etc. are carried out according to the known procedures.

The invention is explained by the following examples, but it is not limited by them.

EXAMPLE 1

0.1 moles of 1-methoxy-2,6-dinitro-4-t-butylbenzene as the compound represented by general formula [I] and 1.5 moles of isopropyl alcohol as the compound represented by the general formula [II] are reacted with stirring at 80° C. for 2 hours in the presence of 0.050 moles of NaOH in a three-necked flask equipped with 200 ml condenser, thermometer and stirrer. Excess isopropanol is removed from the reaction mixture, and the residue is washed with water, the organic layer is extracted from water layer by means of chloroform, and after drying with Glauber's salt chloroform is distilled off. The oily substance remaining is eluted by column chromatography with silica gel as a filler using n-hexane to obtain 0.095 moles of oily substance. The oily substance is confirmed to be the compound represented by the following general formula [III] by its infrared absorption spectrum (referred to IR spectrum hereinafter) and nuclear magnetic resonance spectrum (referred to NMR spectrum hereinafter).

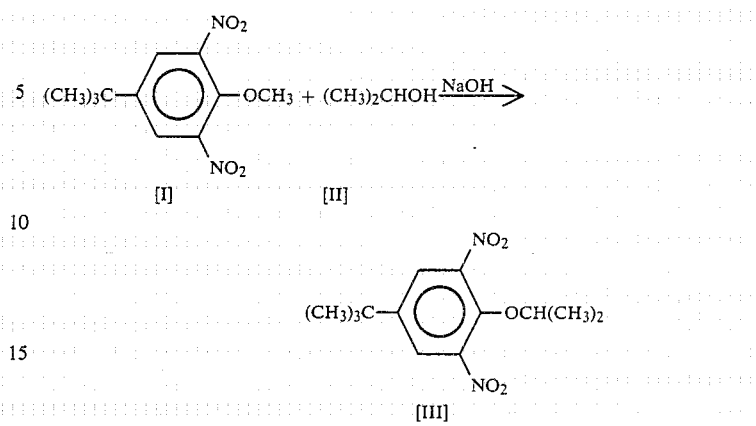

EXAMPLE 2

The reaction and after-treatment are carried out as in Example 1, except that 1-methoxy-2,6-dinitro-4-sec.-butyl benzene as the compound represented by general formula [I], sec.-butyl alcohol as the compound represented by general formula [II] and K$_2$CO$_3$ as the catalyst are used. 0.094 moles of red oily objective compound is obtained. By the analysis of IR and NMR spectra, the oily compound is confirmed to be the compound represented by the following general formula [III].

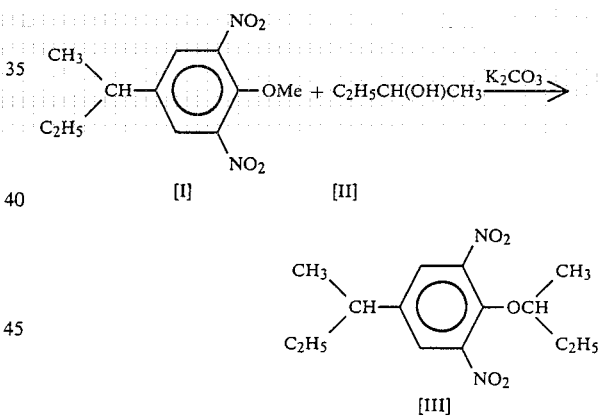

COMPARATIVE EXAMPLE 1

0.1 moles of 1-chloro-2,6-dinitro-4-sec.-butyl benzene and 1.5 moles of sec.-butyl alcohol are reacted in the presence of 0.05 moles of K$_2$CO$_3$ at 80° C. for 4 hours in a similar reactor to the one used in Example 1. The after-treatment of reaction liquid is carried out as in Example 1 to obtain 0.062 moles of oily objective compound (the following general formula [III]).

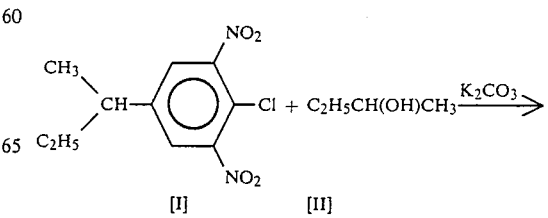

-continued

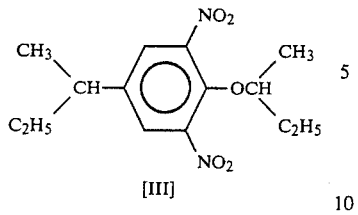

[III]

COMPARATIVE EXAMPLE 2

The procedure is the same as in Comparative example 1, except that 2,6-dinitro-4-sec.-butyl phenol is used instead of 1-methoxy-2,6-dinitro-4-sec.-butyl benzene, and sec.-butyl chloride is used instead of sec.-butanol. 0.049 moles of oily objective compound (the following general formula [III]) is obtained.

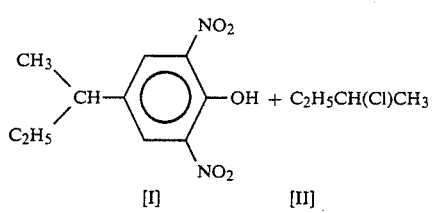

[I]      [II]

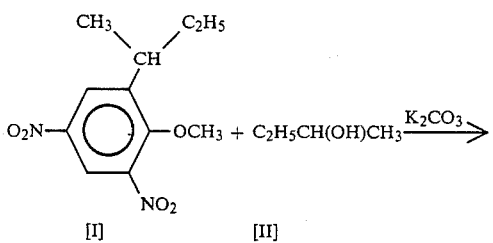

[III]

EXAMPLE 3

The reaction and after-treatment are carried out as in Example 1, except that 1-methoxy-2,4-dinitro-6-sec.-butyl benzene as the compound represented by general formula [I], sec.-butanol as the compound represented by general formula [II] and $K_2CO_3$ as the catalyst are used. 0.096 moles of light yellow colored oily objective compound is obtained. By analysis of IR and NMR spectra, the oily compound is confirmed to be the compound represented by the following general formula [III].

$$O_2N-\underset{NO_2}{\underset{|}{\overset{CH_3\diagdown \diagup C_2H_5}{\overset{CH}{\bigcirc}}}}-OCH_3 + C_2H_5CH(OH)CH_3 \xrightarrow{K_2CO_3}$$

[I]      [II]

-continued

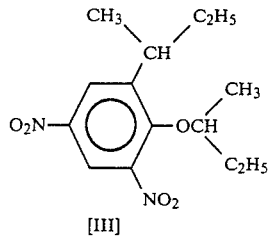

[III]

EXAMPLES 4~14

By carrying out each of the reactions under the reaction conditions shown in Table 1 reported later (including the designations of each of the radicals $R_1$, $R_2$ and $R_3$) in the reaction according to the invention represented by the following equation, the results shown in the table are obtained respectively.

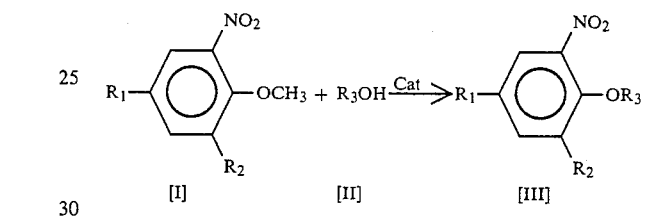

[I]      [II]      [III]

COMPARATIVE EXAMPLES 3~6

By carrying out each of the reactions under the reaction conditions shown in Table 3 reported later (including the designations of each radicals $R_1$, $R_2$ and $R_3$) in the known process represented by the following equation, the results shown in the table are obtained respectively.

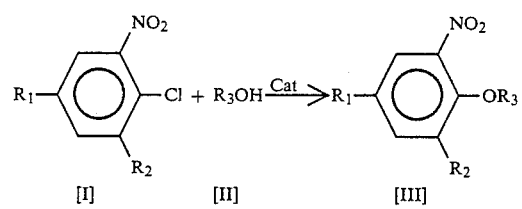

[I]      [II]      [III]

COMPARATIVE EXAMPLES 7 AND 8

By carrying out each of the reactions under the reaction conditions shown in Table 3 reported later (including the designations of each radicals $R_1$, $R_2$ and $R_3$) in the known process represented by the following equation, the results shown in the table are obtained respectively.

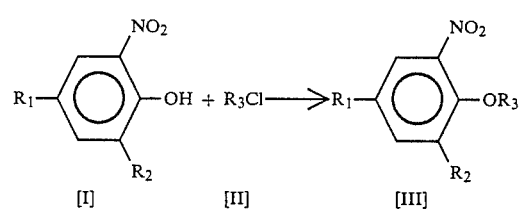

[I]      [II]      [III]

TABLE 1
Examples 4~14

| Example No. | Types of R — R₁ | R₂ | R₃ (OH) | Catalyst Type | Quantity in mole | Solvent | Temp. (°C.) | Time (hrs) | Yield of [III] in % | Properties |
|---|---|---|---|---|---|---|---|---|---|---|
| 4 | CH₃— | NO₂ | Et(OH) | NaOH | ½ | — | 70 | 2.0 | 96 | oily |
| 5 | ⟨H⟩— | " | (HO)—⟨H⟩+ | NaOH | ½ | toluene | 140 | 2.0 | 87 | mp 129~130 |
| 6 | NO₂ | sec-butyl | ⟨H⟩—(OH) | KOH | ¼ | — | 90 | 2.0 | 92 | oily |
| 7 | sec-butyl | NO₂ | ⟨○⟩—CH₂CH₂CH₂(OH) | K₂CO₃ | " | toluene | 130 | 3.0 | 94 | " |
| 8 | NO₂ | Et | ⟨○⟩—CH₂(OH) | pyridine | ⅓ | — | 100 | 4.0 | 90 | " |
| 9 | sec-butyl | NO₂ | CH₂CH₂CH₂(OH) | K₂CO₃ | " | benzene | 80 | 4.0 | 85 | " |
| 10 | " | " | ⟨○⟩—(OH) | pyridine | ¼ | toluene | 130 | 4.0 | 87 | mp 104~105 |
| 11 | " | " | Cl-⟨○⟩-(OH), Cl | NaOH | ⅓ | " | " | 3.5 | 84 | mp 80~81 |
| 12 | " | " | CH₃-⟨○⟩-(OH), Cl | " | " | " | " | 4.0 | 87 | mp 117~118 |
| 13 | " | " | ⟨○⟩-(OH), OEt | KOH | " | " | 100 | " | 82 | mp 90~91 |
| 14 | " | " | Me, Cl-⟨○⟩-(OH), Me | NaOH | " | xylene | 140 | 2.0 | 84 | mp 102~103 | mp: melting point

TABLE 2
Comparative examples 3~6

| Example No. | Types of R — R₁ | R₂ | R₃ (OH) | Catalyst Type | Quantity in mole | Solvent | Temp. (°C.) | Time (hrs) | Yield of [III] in % | Properties |
|---|---|---|---|---|---|---|---|---|---|---|
| 3 | sec-butyl | NO₂ | ⟨○⟩—(OH) | NaOH | ½ | toluene | 130 | 4.0 | 0 | |
| 4 | " | " | " | pyridine | " | " | 110 | 6.0 | 52 | mp 104~105 |
| 5 | " | " | O₂N—⟨○⟩—(OH), Cl | KOH | 1.0 | " | 130 | " | 0 | |
| 6 | " | " | " | pyridine | 5.0 | — | 120 | 4.0 | 61 | mp 117~118 |

TABLE 3

| Example No. | Types of R | | | Catalyst | | Reaction conditions | | | Results | |
|---|---|---|---|---|---|---|---|---|---|---|
| | $R_1$ | $R_2$ | $R_3$ (Cl) | Type | Quantity in mole | Solvent | Temp. (°C.) | Time (hrs) | Yield of [III] in % | Properties |
| Comparative examples 7 and 8 | | | | | | | | | | |
| 7 | sec-butyl | $NO_2$ | 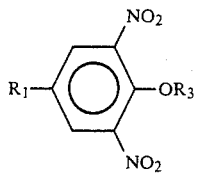 | pyridine | 5.0 | — | 120 | 4.0 | 0 | |
| 8 | sec-butyl | " | 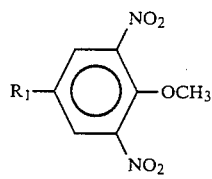 | " | " | " | " | 6.0 | 0 | |

What is claimed is:

1. A process for producing a dinitrophenyl ether of the formula $$R_1\text{-}\underset{NO_2}{\underset{|}{\overset{NO_2}{\overset{|}{C_6H_3}}}}\text{-}OR_3$$

wherein $R_1$ represents a member selected from the group consisting of methyl, sec.-butyl, t-butyl and cyclohexyl, and $R_3$ represents a member selected from the group consisting of ethyl, propyl, isopropyl, sec.-butyl, t-butylcyclohexyl, phenylpropyl, phenyl, 3,5-dichlorophenyl, 2-chloro-4-methyl-phenyl 2-ethoxyphenyl, and 3,5-dimethyl-4-chloro-phenyl, which process comprises reacting a compound of the formula $$R_1\text{-}\underset{NO_2}{\underset{|}{\overset{NO_2}{\overset{|}{C_6H_3}}}}\text{-}OCH_3$$

wherein $R_1$ is as defined above, with a compound of the formula $R_3OH$ wherein $R_3$ is as defined above, in the presence of an alkaline compound.

2. A process according to claim 1 wherein said reaction is carried out in the presence of an inert solvent.

3. A process according to claim 1 wherein said reaction is carried out in the absence of an inert solvent.

* * * * *